United States Patent [19]
Pitts et al.

[11] Patent Number: 5,368,568
[45] Date of Patent: Nov. 29, 1994

[54] DISABLING HYPODERMIC SYRINGE

[76] Inventors: Raymond H. Pitts, 6020 4th St., S., St. Petersburg, Fla. 33705; Susan J. Schneider; Meri L. Huckins, both of 1399 S. Belcher Rd., Lot #112, Largo, Fla. 34641

[21] Appl. No.: 134,625

[22] Filed: Oct. 12, 1993

[51] Int. Cl.⁵ ............................................. A61M 5/00
[52] U.S. Cl. .................... 604/110; 604/198; 604/263
[58] Field of Search .............. 604/110, 198, 192, 187, 604/263, 218

[56] References Cited

U.S. PATENT DOCUMENTS

| | | | |
|---|---|---|---|
| 4,850,977 | 7/1989 | Bayless | 604/198 |
| 4,850,994 | 7/1989 | Zerbst et al. | 604/198 |
| 4,863,434 | 9/1989 | Bayless | 604/198 |
| 4,863,435 | 9/1989 | Sturman et al. | 604/198 |
| 4,911,693 | 3/1990 | Paris | 604/192 |
| 4,915,702 | 4/1990 | Haber | 604/198 |
| 4,973,316 | 11/1990 | Dysarz | 604/195 |
| 5,057,086 | 10/1991 | Dillard, III et al. | 604/198 X |
| 5,147,303 | 9/1992 | Martin | 604/110 |
| 5,151,088 | 9/1992 | Allison et al. | 604/192 |
| 5,176,656 | 1/1993 | Bayless | 604/198 |
| 5,201,720 | 4/1993 | Borgia et al. | 604/263 X |

*Primary Examiner*—John D. Yasko
*Attorney, Agent, or Firm*—Crossetta & Associates

[57] ABSTRACT

The invention relates to a hypodermic syringe with needle comprising a spring loaded needle sheath, arranged to be automatically engaged at completion of dosing, which releases to be propelled to a position covering the tip of the needle. The syringe further comprises means for breaching the medicament storage chamber of the hypodermic syringe so that it becomes unusable for intentional reuse.

20 Claims, 1 Drawing Sheet

U.S. Patent      Nov. 29, 1994      5,368,568
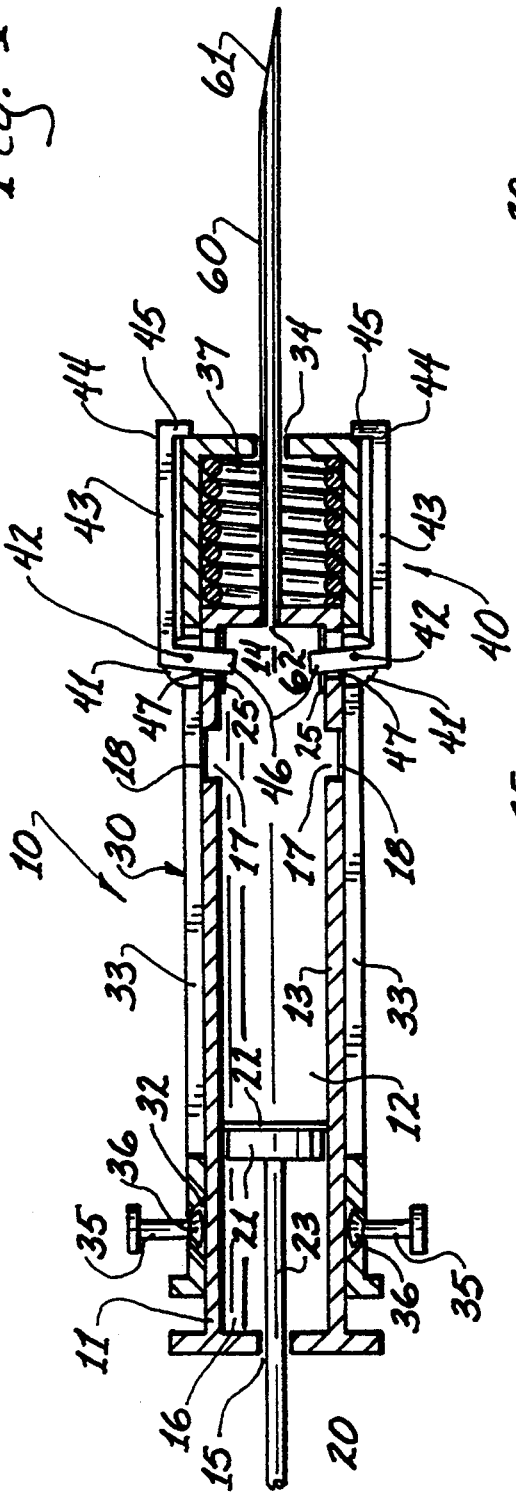
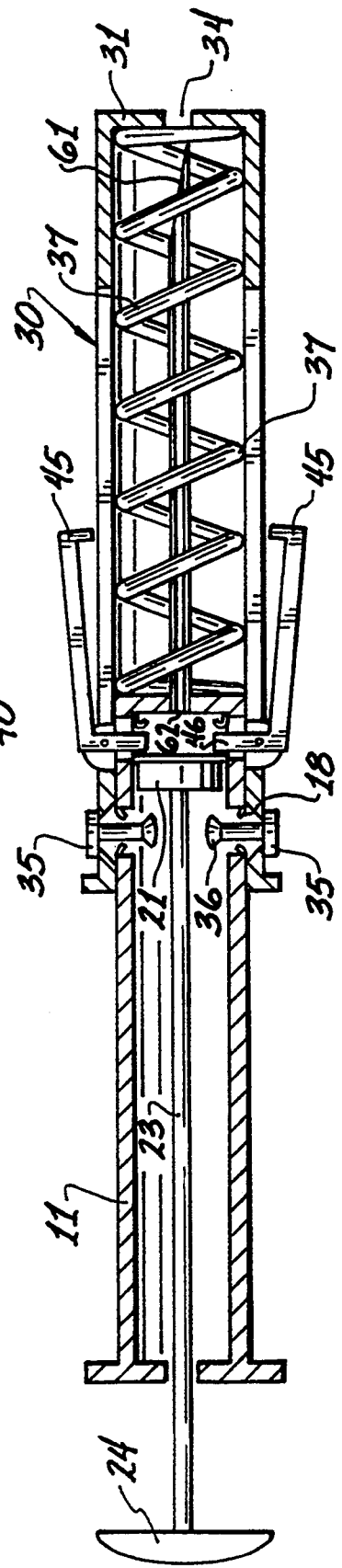

DISABLING HYPODERMIC SYRINGE

This invention relates to hypodermic syringes with needles and most particularly to hypodermic syringes which can be easily disabled, having needles which are automatically protectively sheathed after use.

BACKGROUND OF THE INVENTION

Hypodermic syringes with needles are widely available and enjoy extensive use throughout industry, particularly in the field of medicine wherein they are commonly employed for injecting medicaments, drugs, inoculants and the like into an array of human or other patients.

Generally a hypodermic syringe is a device comprising a medicament storage compartment having a means, such as a movable plunger, suitably arranged for filling and expelling fluids to and from the storage compartment though a common inlet/outlet. Hypodermic syringes are generally fitted with a hollow needle having a dosing outlet at a distal end, which needle is arranged contiguous with the common inlet/outlet of the storage compartment to facilitate directing fluid flow to or from a specific site. In order to expedite their use and ease pain associated with animal injections, needles have been so improved that the modern needle comprises a tip which can effortlessly pierce barriers such as the skin and it is generally understood that extreme care must be taken to avoid inadvertent or undesirable skin penetration by the needle.

Unfortunately, the widespread use of hypodermic syringes with needles and the effortless manner in which such needles can penetrate the skin barrier are prime factors contributing to their misuse and thus pose a continuing problem to their safe use. For example, it is not unusual for persons using such devices to accidentally prick themselves or others with an exposed needle tip of a hypodermic syringe through carelessness. It is not unusual for such devices to be improperly discarded or otherwise carelessly placed such that an unsuspecting person is inadvertently pricked. The discarding of used hypodermic syringes with needles is a particular problem in that inadvertent needle pricks and/or the intentional improper reuse of such devices are a continuing threat and can be a devastating disease transmission source.

The prior art is replete with disclosure of improved hypodermic syringes with needle, many of which provide elaborate arrangements to protect from accidental pricking after use of the device. Some such devices comprise needle sheathing arrangements which are effective in preventing accidental pricking, but require careful manipulation by the user to enable sheathing and have generally not enjoyed commercial success. Other devices provide various means which automatically engage effective sheathing means upon use of the device, but generally such sheathing means are easily defeated by the determined intentional re-user, and the risk of careless reuse, with the inherent problem of disease transmission, remains a continuing problem.

An object of the present invention is to provide a novel hypodermic syringe with needle that automatically protectively engages the dosing end of the needle upon use.

Another object of the invention is to provide a novel sheathing arrangement for a hypodermic syringe with needle that is difficult to intentionally defeat.

A further object of the invention is to provide a novel hypodermic syringe with needle that conveniently and safely disables the syringing capability of the device.

A still further object of the invention is to provide a novel disposable hypodermic syringe with needle that disables and automatically sheathes the needle upon a single use.

These and other objects of the invention will be apparent from the following description of the invention.

SUMMARY OF THE INVENTION

The present invention relates to a hypodermic syringe with needle comprising a safety tip release mechanism, arranged to be automatically engaged at completion of dosing, which releases a spring-loaded safety tip to be propelled to a position covering the dosing tip of the needle. The syringe further comprises means for breaching the medicament storage chamber of the hypodermic syringe, which becomes enabled upon release of the safety tip, so that the syringe becomes unusable for intentional reuse.

In one embodiment, the device of the invention comprises a generally cylindrical medicament storage chamber having an outlet at a first end which is in fluid communication with a hollow needle which in turn has a dosing opening at a distal end thereof. A spring loaded safety tip is arranged to encircle the needle and upon release from a spring loaded state is propelled by the spring, along the length of the needle, to a safety state wherein the safety tip shields the tip of the needle at the distal end thereof from inadvertent contact. The medicament storage chamber comprises an axially movable plunger assembly, arranged to sealingly engage an interior wall of the chamber, which upon axial movement within the chamber toward the outlet, expels fluid from said storage compartment, through said outlet, through said hollow needle and said dosing opening at said distal end thereof.

The embodiment further comprises one or more means for releasing said safety tip from said spring-loaded state, which is actuatably associated with movement of said plunger assembly. In a preferred embodiment, said means for releasing comprises a pivot release means. The pivot release means generally comprises an elongate pivot member having first and second ends arranged about a pivot. The first end of said pivot member is arranged to engage and hold the safety tip in a loaded state when it is at a first pivot position and release the safety tip from a loaded state when it is pivoted to a second pivot position. The second end of said pivot member is arranged to engage the plunger assembly when the plunger reaches a predetermined position in axial movement, preferably at completion of expulsion of medicament from the medicament storage chamber during dosing, and causes the first end of said pivot member to move about the pivot from said first pivot position to said second pivot position.

The device further comprises means for breaching the integrity of the medicament chamber, and is arranged to form an opening in the medicament storage compartment to atmosphere at or about release of the safety tip from its loaded state. Such opening discourages re-use of the device by intentionally defeating suction filling capability of the medicament storage compartment through reverse axial movement of the plunger. The opening also generally enables fluid leakage from the chamber which defeats further storage of fluids therein.

In a preferred embodiment of the device, wherein a pivotable release means comprises an elongate pivot member having first and second ends arranged to pivot about an axle, the axle is arranged such that the pivot member extends through a sealed opening in the medicament chamber wall to the interior of the storage chamber for engagement of the second end with the plunger assembly. Suitable engagement of the second end of the pivot member with the plunger causes the movement of the pivot member which causes the seal to be breached and creates an opening in the storage compartment to atmosphere. The opening defeats vacuum filling and/or enables leakage of fluid from the medicament storage chamber.

In a further preferred embodiment the sealing means comprises a thin foil, wax, tape, elastomeric material or the like which sealingly engages an opening through which the pivot member extends into the medicament chamber and which is arranged to tear or otherwise be breached or the like to create an opening to the interior of the chamber with appropriate movement of the pivot member.

In a further preferred embodiment the first end of the pivoting member comprises a latch which engages the safety tip in the loaded state and disengages the safety tip during release.

The safety tip generally comprises a protective end piece having a centralized hole therein through which the needle extends when the safety tip is in a loaded state. The hole is generally sized minimally larger than the diameter of the needle and the safety tip is arranged to extend to or about the end of the needle at the safety state. A coil spring is generally arranged between the protective end and the body of the syringe and means are provided which hold the safety tip with spring compressed toward the syringe body in a spring loaded state. In a preferred arrangement, the coil spring is arranged such that when the safety tip reaches the safety state, the tip of the needle moves from alignment with the hole in the protective end such that the needle cannot easily be re-directed through the hole.

In a further embodiment, the safety tip comprises a hollow sheath, having a protective end, that at least partially shields the body of the needle when extended to the safety position. In a preferred embodiment, a sheath is arranged to telescope over the body of the hypodermic syringe when the tip is in the spring loaded state. In one embodiment the sheath comprises two or more distinct elongate members which are arranged to extend from the protective end of the safety tip to the hypodermic syringe when the tip is in the safety state. A coil spring is positioned about an elongate member between the syringe and the protective end arranged such that it can be compressed to place the safety tip is in a spring loaded state.

In a further preferred embodiment a coil spring is arranged to generally encircle the needle and is positioned between the syringe and the protective end of a sheath such that it can be compressed to place the safety tip is in a spring loaded state. In a particularly preferred embodiment, a sheath comprises a release slot partially along its longitudinal length to accommodate a pivot release means. In another preferred arrangement a sheath contains one or more lock members, arranged to extend through a wall of elongate members thereof at an end opposite the protective end, which upon extension of the tip to the safety position align with pre-determined breachable location(s), preferably sealed openings, to the interior of the medicament storage chamber. The lock members are arranged such that at extension of the sheath to the safety state, the lock members can be urged through the breachable location(s) into the medicament storage compartment thus breaching the integrity of the medicament storage compartment and locking the sheath from movement away from the safety position.

It should be understood that the broad disclosure of the invention contemplates diverse means for releasing the safety tip to a safety position and diverse means for breaching the integrity of the medicament storage chamber.

BRIEF DESCRIPTION OF THE DRAWINGS

FIG. 1 is a side elevation sectional view of a hypodermic syringe of the invention with needle exposed.

FIG. 2 is a side elevation sectional view of the hypodermic syringe of FIG. 1 showing the sheath in protective covering relation about the needle.

DETAILED DESCRIPTION OF THE DRAWINGS

Referring now to FIGS. 1 and 2 wherein is illustrated a preferred embodiment of the invention comprising a syringe with needle configured for disposal after single use.

Therein, hypodermic syringe 10, comprising generally cylindrical main body 11, having a medicament storage chamber 12 comprising dosing end 14, fitted with hollow needle 60 which comprises a dosing outlet 61 and medicament inlet 62 which is in fluid communication with medicament storage chamber 12 of main body 11. Medicament storage chamber 12 is illustrated as comprising generally cylindrical wall 13, being in fluid communication at end 14 with medicament inlet 62 and comprising an opening 15 at another end 16 through which rod 23 of plunger assembly 20 extends.

Plunger assembly 20 generally comprises plunger head 21, seal 22 which is arranged to sealingly engage the interior surface of cylindrical wall 13 of storage chamber 12, and rod 23 having thumb platform 24 at a distal end thereof. Plunger assembly 20 is arranged to be axially moveable within storage chamber 12 with seal 22 sealingly engaging cylindrical wall 13 of storage chamber 12 and enabling the movement of fluid from and to storage chamber 12 through hollow needle 60.

Sheath 30, is arranged about cylindrical main body 11 and is coaxially aligned therewith and axially extensible relative to main body 11 such that sheath 30 is adapted for movement between a retracted position as illustrated in FIG. 1 and an axially extended position as illustrated in FIG. 2. Sheath 30 is illustrated as generally comprising protective end 31 and conical lock holes 32, at a distal end, which comprise lock members 35 mounted to enable inward and outward movement, release slots 33 and spring 37.

Lock members 35 are mounted through lock holes 32 with ends 36 thereof being configured to restrict outward movement of the lock members upon engaging the conical surface of lock holes 32 at a desirable maximum position of outward movement and to enable axially movement of sheath 30 relative to main body 11 at such maximum position. Lock holes 32 are positioned to align with breachable openings 17 comprising seals 18 of main body 11 when sheath 30 is in the extended position illustrated in FIG. 2.

Pivot release assembly 40 generally comprises pivot support 41, pivot axle 42, and pivot member 43 which are cooperatively arranged at dosing end 14 of main body 11 to enable release of sheath 30 to an extended position upon activation by plunger assembly 20. Pivot member 43 comprises a first end 44 having a latch means 45 which engages protective end 31 of sheath 30 in a retracted position. Another end 46 of pivot member 43 is arranged beyond pivot axle 42 to extend through release holes 47 comprising foil seals 25 of main body 11 into the path of plunger assembly 20 during its axial movement within storage chamber 12.

In the use of the illustrated hypodermic syringe with needle, the needle is generally provided for use with the sheath in the retracted position shown in FIG. 1 and the storage chamber comprising the desired medicament in the desired dosage. The sheath is locked in the retracted position by the latches at the first end of the pivot member and seals 18 and 25 prevent leakage of fluid from the storage chamber by maintaining its structural integrity. Locking members 35 are in an outward position. The needle is inserted into the patient and the administrator thereof pushes the thumb platform of the plunger forcing the plunger assembly to move axially through the storage chamber pushing the medicament from the chamber through the hollow needle into the patient. When the plunger assembly engages and moves end 46 of the pivot member, end 44 is caused to move outwardly and disengages latches 45 from the safety tip of the sheath which in turn allows the safety tip to be propelled along the needle by the coiled spring the length of slots 33 to its extended position. The movement of end 46 in turn tears or otherwise breaches seal 25 which defeats the structural integrity of chamber 12. The reaching of an extended position by the sheath aligns lock members 35 with sealed openings 17 to the medicament chamber. Urging lock members 35 inwardly tears or otherwise breaches seals 18 and fixes the locking members to resist reverse axial movement by the plunger assembly.

We claim:

1. In a hypodermic syringe comprising a hollow needle in fluid communication with a medicament storage chamber and having a plunger assembly arranged for expelling medicament through an opening at a distal end of said needle by axial movement of a plunger within said medicament chamber, the improvement comprising:
a safety tip, comprising a protective end having an opening therein, said safety tip being mounted to said needle through said opening in said protective end and being arranged to enable axial movement of said safety tip from a first position wherein said distal end of said needle extends through said opening of said safety end, to a second position wherein said distal end of said needle is shielded by said protective end of said safety tip;
a spring, arranged to propel said safety tip from said first position to said second position;
means for releasably retaining said safety tip in said first position, said means being arranged to engage said plunger assembly, within said chamber, at a point in axial movement of said plunger and release said safety tip from said first position to said second position wherein said distal end of said needle is shielded by said protective end of said safety tip.

2. The syringe of claim 1 wherein said safety tip comprises a hollow sheath, arranged to telescope from a first position about said hypodermic syringe to a second position wherein said protective end shields said distal end of said needle.

3. The syringe of claim 1 wherein a spring is coiled about said needle in an arrangement to propel said safety tip from said first position to said second position.

4. The syringe of claim 1 wherein a spring is coiled adjacent said needle in an arrangement to propel said safety tip from said first position to said second position.

5. The syringe of claim 1 wherein said means for releasably retaining said safety tip comprises a release means, arranged to engage said plunger at a point in axial movement of said plunger and release said safety tip from said first position to said second position.

6. The syringe of claim 1 wherein said means for releasably retaining said safety tip comprises an elongate member arranged about a pivot, said elongate member having a first end arranged to engage and releasably retain said safety tip in said first position and having a second end arranged to engage said plunger assembly at a point in said axial movement thereof.

7. The syringe of claim 1 wherein said means for releasable retaining said safety tip is arranged to extend through a wall of said medicament storage chamber and engage said plunger assembly.

8. The syringe of claim 7 wherein said means for releasably retaining said safety tip extends through an opening in said wall of said storage chamber, said opening being secured by a breachable sealing means.

9. The syringe of claim 8 wherein said breachable sealing means comprises foil, tape or wax.

10. The syringe of claim 6 wherein said elongate member comprises a first end having latch means for retaining said safety tip in said first position.

11. The syringe of claim 10 wherein said elongate member comprises an end arranged to extend through an opening in a wall of said storage chamber for engaging a plunger.

12. The syringe of claim 6 wherein said pivot comprises an axle.

13. The syringe of claim 1 comprising means for locking said safety tip in said second position.

14. The syringe of claim 2 comprising means for locking said sheath in said second position, comprising members which are arranged to be urged through an opening of a wall of said storage chamber when said sheath is in said second position.

15. The syringe of claim 14 wherein said opening of a wall comprises sealing means.

16. The syringe of claim 1 wherein at said second position said distal end of said needle is positioned adjacent said opening in said protective end.

17. The syringe of claim 2 wherein said hollow sheath comprises a slot, being dimensioned such that an end wall thereof engages said releasable retaining means at said second position of said protective end.

18. A hypodermic syringe comprising:
a hollow needle in fluid communication with a medicament storage chamber;
a plunger, arranged for expelling medicament through an opening at a distal end of said needle by axial movement of said plunger within said medicament chamber;
a hollow sheath, comprising a protective end having an opening therein and mounted to said needle through said opening, said sheath being arranged to telescope axially from a first position 19. The syringe of claim 18 comprising means for locking said sheath in said second position, said means for locking comprising members which are arranged to be urged through an opening of a wall of said storage chamber when said sheath is in said second position.

20. The syringe of claim 18 wherein said means for releasably retaining said sheath is arranged to extend through a sealed opening in a wall of said storage chamber and engage said plunger.

* * * * *